(12) United States Patent
Moss et al.

(10) Patent No.: US 7,528,151 B2
(45) Date of Patent: May 5, 2009

(54) HETEROCYCLIC UREA DERIVATIVES FOR THE TREATMENT OF PAIN

(75) Inventors: Stephen Frederick Moss, Harlow (GB); Harshad Kantilal Rami, Harlow (GB); Mervyn Thompson, Harlow (GB); David Richard Witty, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 535 days.

(21) Appl. No.: 10/548,260

(22) PCT Filed: Mar. 5, 2004

(86) PCT No.: PCT/GB2004/000978

§ 371 (c)(1),
(2), (4) Date: Sep. 6, 2005

(87) PCT Pub. No.: WO2004/078749

PCT Pub. Date: Sep. 16, 2004

(65) Prior Publication Data

US 2007/0117820 A1    May 24, 2007

(30) Foreign Application Priority Data

Mar. 6, 2003 (GB) ................... 0305165.3
Jul. 15, 2003 (GB) ................... 0316554.5

(51) Int. Cl.
C07D 401/14 (2006.01)
C07D 401/12 (2006.01)
A61K 31/4725 (2006.01)

(52) U.S. Cl. ...................... 514/310; 546/143

(58) Field of Classification Search ................ 544/128, 544/331; 546/143; 514/235.2, 256, 275, 514/310
See application file for complete search history.

(56) References Cited

U.S. PATENT DOCUMENTS

| | | | |
|---|---|---|---|
| 5,925,635 | A | 7/1999 | Maduskuie, Jr. et al. |
| 6,355,631 | B1 | 3/2002 | Achard et al. |
| 6,506,572 | B2 | 1/2003 | Biedermann et al. |
| 6,602,882 | B1 | 8/2003 | Davies et al. |
| 6,723,730 | B2 | 4/2004 | Bakthavatchalam et al. |
| 6,903,085 | B1 | 6/2005 | Thom et al. |
| 2003/0153568 | A1 | 8/2003 | Cusack et al. |
| 2004/0082661 | A1 | 4/2004 | Rami et al. |
| 2004/0171639 | A1 | 9/2004 | Rami et al. |
| 2005/0113414 | A1 | 5/2005 | Watson et al. |

FOREIGN PATENT DOCUMENTS

| | | |
|---|---|---|
| DE | 28 16 884 | 11/1978 |
| DE | 199 55 794 | 5/2000 |
| EP | 0416581 | 3/1991 |
| EP | 0591030 | 4/1994 |
| EP | 0625507 | 11/1994 |
| EP | 0628310 | 12/1994 |
| ES | 2007808 | 7/1989 |
| WO | WO00/71171 | 11/2000 |
| WO | WO01/07409 | 2/2001 |
| WO | WO03/022809 | 3/2003 |
| WO | WO03/072545 | 9/2003 |
| WO | WO2004/024710 | 3/2004 |
| WO | WO2004/026836 | 4/2004 |
| WO | WO2004/078101 | 9/2004 |
| WO | WO2004/078744 | 9/2004 |

OTHER PUBLICATIONS

Ulrich, Chapter 4: Crystallization, Kirk-Othmer Encyclopedia of Chemical Technology, Aug. 2002.*
Vippagunta et al., Cyrstalline Solids, Advanced Drug Delivery Reviews, 48, pp. 3-26, 2001.*
West, Solid Solutions, Solid State Chemistry and its applications, pp. 358 & 365, 1988.*
Valenzano et al., PubMed Abstract (Curr Med Chem. 11(24):3185-202) Dec. 2004.*
Szallasi et al., Vanilloid Receptor TRPV1 Antagonists as the Next Generation of Painkillers—Miniperspective, Journal of Medicinal Chemistry, vol. 47, No. 11, pp. 2717-2723, May 2004.*
Frigola et al., *Journal of Medicinal Chemistry*, vol. 36 No. 7 1993 pp. 801-810.
Carling et al., *Journal of Medicinal Chemistry*, vol. 42 No. 14 (1999) pp. 2706-2715.
Huang et al., *Journal of Medicinal Chemistry*, vol. 41 No. 13 (1998) pp. 2361-2370.
Huang et al., *Journal of Medicinal Chemistry*, vol. 44 No. 25 (2001) pp. 4404-4415.

* cited by examiner

*Primary Examiner*—Deepak Rao
(74) *Attorney, Agent, or Firm*—Reid S. Willis; Charles M. Kinzig

(57) ABSTRACT

Compounds of formula (I):

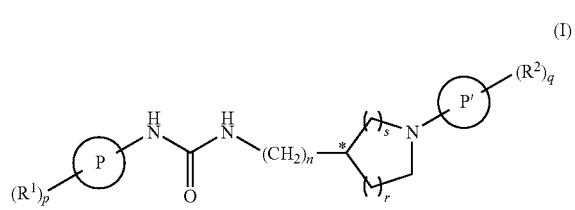

or a pharmaceutically acceptable salt thereof, or a solvate thereof, wherein: P, P', $R^1$, $R^2$, n, p, q, r, and s are as defined in the specification, processes for preparing such compounds, pharmaceutical compositions comprising such compounds and their use in therapy.

6 Claims, No Drawings

HETEROCYCLIC UREA DERIVATIVES FOR THE TREATMENT OF PAIN

This application is a 371 of PCT/GB04/00978 filed Mar. 5, 2004.

This invention relates to novel compounds, especially urea derivatives, having pharmacological activity, processes for their preparation, to compositions containing them and to their use in medicine, especially in the treatment of various disorders.

Vanilloids are a class of natural and synthetic compounds that are characterised by the presence of a vanillyl (4-hydroxy 3-methoxybenzyl) group or a functionally equivalent group. Vanilloid Receptor (VR1), whose function is modulated by such compounds, has been widely studied and is extensively reviewed by Szallasi and Blumberg (The American Society for Pharmacology and Experimental Therapeutics, 1999, Vol. 51, No. 2.).

A wide variety of Vanilloid compounds of different structures are known in the art, for example those disclosed in European Patent Application Numbers, EP 0 347 000 and EP 0 401 903, UK Patent Application Number GB 2226313 and International Patent Application, Publication Number WO 92/09285. Particularly notable examples of vanilloid compounds or vanilloid receptor modulators are capsaicin or trans 8-methyl-N-vanillyl-6-nonenamide which is isolated from the pepper plant, capsazepine (*Tetrahedron*, 53, 1997, 4791) and olvanil or —N-(4-hydroxy-3-methoxybenzyl)oleamide (*J. Med. Chem.*, 36, 1993, 2595).

U.S. Pat. Nos. 3,424,760 and 3,424,761 both describe a series of 3-Ureidopyrrolidines that are said to exhibit analgesic, central nervous system, and pyschopharmacologic activities. These patents specifically disclose the compounds 1-(1-phenyl-3-pyrrolidinyl)-3-phenyl urea and 1-(1-phenyl-3-pyrrolidinyl)-3-(4-methoxyphenyl)urea respectively.

International Patent Applications, Publication Numbers WO 02/08221, WO 02/16317, WO 02/16318 and WO 02/16319 each disclose certain vanilloid receptor antagonists and their use in the treatment of diseases associated with the activity of the vanilloid receptor.

International Patent Applications, Publication Numbers WO 02/072536 and WO 02/090326, and International Patent Application, Publication Number WO 03/022809 (published after a priority date of the present application) disclose a series of urea derivatives and their use in the treatment of diseases associated with VR1 activity.

According to a first aspect of the present invention, there is provided a compound of formula (I):

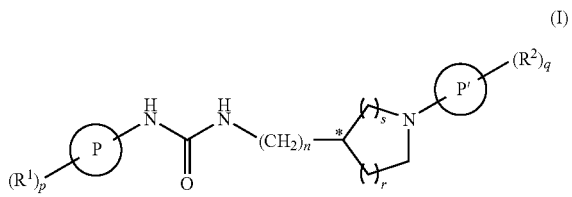

(I)

or a pharmaceutically acceptable salt thereof, or a solvate thereof, wherein:

P represents iso-quinolinyl;
P' is selected from phenyl, pyridinyl, pyrimidinyl and thiazolyl;
$R^1$ and $R^2$ are independently selected from —H, halo, alkyl, alkoxy, cycloalkyl, aralkyl, aralkoxy, cycloalkylalkyl, cycloalkylalkoxy, —CN, —$NO_2$, —OH, —$OCF_3$, —$CF_3$, —$NR^4R^5$, —$S(O)_mR^6$, —$S(O)_2NR^4R^5$, —$OS(O)_2R^6$, —$OS(O)_2CF_3$, —$O(CH_2)_xNR^4R^5$, —$C(O)CF_3$, —$C(O)$alkyl, —$C(O)$cycloalkyl, —$C(O)$aralkyl, —$C(O)Ar$, —$C(O)(CH_2)_xOR^6$, —$C(O)(CH_2)_xNR^4R^5$, —$C(O)$alkoxy, —$C(O)NR^4R^5$, —$(CH_2)_xC(O)$alkoxy, —$(CH_2)_xOC(O)R^6$, —$(CH_2)_xOR^6$, —$(CH_2)_xNR^4R^5$, —$(CH_2)_xC(O)NR^4R^5$, —$(CH_2)_xN(R^4)C(O)R^6$, —$(CH_2)_xS(O)_2NR^4R^5$, —$(CH_2)_xN(R^4)S(O)_2R^6$, -ZAr, —$(CH_2)_xS(O)_2R^6$, —$(OCH_2)_xS(O)_2R^6$, —$N(R^4)S(O)_2R^6$, —$N(R^4)C(O)R^6$ or —$(CH_2)_xC(O)$alkyl;

$R^4$ and $R^5$ may be the same or different and represent H or alkyl or $R^4$ and $R^5$ together with the atoms to which they are attached form a $C_{3-6}$azacycloalkane, $C_{3-6}$(2-oxo)azacycloalkane ring or $C_{5-8}$ polymethylene chain optionally interrupted by heteroatoms;
Z represents a bond, O, S or $NR^7$;
$R^6$ represents alkyl or aryl;
$R^7$ represents hydrogen, alkyl or aryl;
m represents an integer 1 or 2;
n represents an integer 0, 1, 2 or 3;
p and q independently represent an integer 0, 1, 2, 3 or 4;
r represents an integer 1, 2 or 3;
s represents an integer 0, 1 or 2
wherein r+s=2, 3 or 4; and
x represents an integer 0, 1, 2, 3, 4, 5 or 6.

Examples of the $C_{3-6}$azacycloalkane ring that $R^4$ and $R^5$ may independently represent, when taken together with the atoms to which they are attached, include pyrrolidine and piperidine.

Examples of the $C_{3-6}$(2-oxo)azacycloalkane ring that $R^4$ and $R^5$ may independently represent, when taken together with the atoms to which they are attached, include pyrrolidinone and piperidinone.

Examples of the $C_{5-8}$ polymethylene chain optionally interrupted by heteroatoms that $R^4$ and $R^5$ may independently represent when taken together with the atoms to which they are attached, include a $C_{5-8}$ polymethylene chain optionally interrupted by heteroatoms such as O or —$NR^7$. Specific examples include morpholine and piperazine.

When p or q represent 2, 3 or 4 the groups $R^1$ or $R^2$ may be the same or different.

Preferably P represents 5-isoquinolinyl.

In one set of compounds of interest, P' represents phenyl, pyridyl (eg 2-pyridyl) or pyrimidinyl (eg 2-pyrimidinyl). In another set of compounds of interest P' represents thiazolyl (eg 2-thiazolyl). Preferably, P' represents phenyl, 2-pyridyl, 2-pyrimidinyl or 2-thiazolyl. More preferably P' represents 2-pyridyl or 2-pyrimidinyl, especially 2-pyridyl. Other examples of P' include 4-pyrimidinyl, 3-pyridyl and 4-pyridyl.

Preferably $R^1$ represents halo, alkyl, alkoxy, —CN or —$OCF_3$. Preferably, $R^1$ is fluoro, chloro, bromo, methyl, tert-butyl, iso-propoxy, —CN or —$OCF_3$. Most preferably $R^1$ is methyl.

Preferably, p represents 1 or 2.

Preferably, n represents 0 or 1, more preferably 0.

Preferably $R^2$ represents halo, alkyl, alkoxy, —CN or $CF_3$, more preferably chloro, fluoro, bromo, methyl, methoxy, —CN or —$CF_3$. Compounds wherein $R^2$ represents halophenyl (eg fluorophenyl especially p-fluorophenyl) are also of interest. Another example of group $R^2$ is —$CH_2$—N-morpholinyl.

Preferably, q represents 1 or 2.

Preferably, r+s represents 2 or 3, most preferably 3.

Preferably r represents 1. Preferably s represents 1 or 2, more preferably 2.

Preferably, x represents 1, 2 or 3.
Preferably $R^4$ represents methyl or hydrogen
Preferably $R^5$ represents methyl or hydrogen.
Preferably $R^6$ represents methyl.
Preferably $R^7$ represents methyl or hydrogen.
Preferably Z represents a bond.
Preferably the moiety P—$(R^1)_p$ represents 1-methyl-5-isoquinolinyl or 1,3-dimethyl-5-isoquinolinyl.
Specific examples of preferred moiety P'—$(R^2)_q$ are 3-Cl-5-trifluoromethyl-pyrid-2-yl, 5-trifluoromethyl-6-methoxy-pyrid-2-yl and 6-trifluoromethyl-pyrid-2-yl. Other examples include 4-(4-morpholinylmethyl)-6-methyl-pyrid-2-yl.

Compounds of formula (I) of particular interest according to the present invention are Examples 1 to 69 or pharmaceutically acceptable salts or solvates thereof.

Certain of the carbon atoms of formula (I) are chiral carbon atoms, such as the carbon atom marked with an "*", and therefore compounds of formula (I) may exist as stereoisomers. The invention extends to all optical isomers such as stereoisomeric forms of the compounds of formula (I) including enantiomers and mixtures thereof, such as racemates. The different stereoisomeric forms may be separated or resolved one from the other by conventional methods or any given isomer may be obtained by conventional stereospecific or asymmetric syntheses.

Preferred compounds of formula (I) have the C* carbon in the R-configuration.

Certain of the compounds herein can exist in various tautomeric forms and it is to be understood that the invention encompasses all such tautomeric forms.

As indicated above, the compounds of formula (I) can form salts, especially pharmaceutically acceptable salts. Suitable pharmaceutically acceptable salts are those use conventionally in the art and include those described in *J. Pharm. Sci.*, 1977, 66, 1-19, such as acid addition salts.

Suitable pharmaceutically acceptable salts include acid addition salts.

Suitable pharmaceutically acceptable acid addition salts include salts with inorganic acids such, for example, as hydrochloric acid, hydrobromic acid, orthophosphoric acid or sulphuric acid, or with organic acids such, for example as methanesulphonic acid, toluenesulphonic acid, acetic acid, propionic acid, lactic acid, citric acid, fumaric acid, malic acid, succinic acid, salicylic acid, maleic acid, glycerophosphoric acid or acetylsalicylic acid.

The salts and/or solvates of the compounds of the formula (I) which are not pharmaceutically acceptable may be useful as intermediates in the preparation of pharmaceutically acceptable salts and/or solvates of compounds of formula (I) or the compounds of the formula (I) themselves, and as such form another aspect of the present invention.

The compounds of formula (I) may be prepared in crystalline or non-crystalline form, and if crystalline, may be optionally hydrated or solvated. This invention includes in its scope stoichiometric hydrates as well as compounds containing variable amounts of water.

Suitable solvates include pharmaceutically acceptable solvates, such as hydrates.

Solvates include stoichiometric solvates and non-stoichiometric solvates.

As used herein the term "alkyl" as a group or part of a group refers to a straight or branched chain saturated aliphatic hydrocarbon radical containing 1 to 12 carbon atoms, suitably 1 to 6 carbon atoms. Such alkyl groups in particular include methyl ("Me"), ethyl ("Et"), n-propyl ("Pr$^n$"), iso-propyl ("Pr$^i$"), n-butyl ("Bu$^n$"), sec-butyl ("Bu$^s$"), tert-butyl ("Bu$^t$"), pentyl and hexyl. The term "cycloalkyl" as part of a group refers to a saturated alicyclic hydrocarbon radical containing containing 3 to 12 carbon atoms, suitably 3 to 6 carbon atoms. Where appropriate, such alkyl groups may be substituted by one or more groups selected from halo (such as fluoro, chloro, bromo), —CN, —CF$_3$, —OH, —OCF$_3$, $C_{2-6}$ alkenyl, $C_{3-6}$ alkynyl, $C_{1-6}$ alkoxy, aryl and di-$C_{1-6}$ alkylamino. Preferably alkyl is unsubstituted.

As used herein, the term "alkoxy" as a group or part of a group refers to an alkyl ether radical, wherein the term "alkyl" is defined above. Such alkoxy groups in particular include methoxy, ethoxy, n-propoxy, iso-propoxy, n-butoxy, iso-butoxy, sec-butoxy and tert-butoxy. Where appropriate, such alkoxy groups may be substituted by one or more groups selected from halo (such as fluoro, chloro, bromo), —CN, —CF$_3$, —OH, —OCF$_3$, $C_{1-6}$ alkyl, $C_{2-6}$ alkenyl, $C_{3-6}$ alkynyl, aryl and di-$C_{1-6}$ alkylamino. Preferably alkoxy is unsubstituted.

As used herein, the term "aryl" as a group or part of a group refers to a carbocyclic aromatic radical ("Ar"). Suitably such aryl groups are 6 membered monocyclic groups or 8-10 membered fused bicyclic groups (including aromatic ring systems fused with non-aromatic ring systems), especially phenyl ("Ph"), biphenyl, indene and naphthyl, particularly phenyl.

Aryl groups contained within moieties $R^1$, $R^2$, $R^6$ or $R^7$ may optionally be substituted (and in the case of bicyclic groups containing an aromatic system fused with a non-aromatic systems may optionally be substituted on either or both of the aromatic and the non-aromatic portion) with one or more substituents selected from the list consisting of halo, hydroxy, carbonyl, alkoxy, alkyl, —CF$_3$, NR$^4$R$^5$ and —SO$_2$R$^6$.

The term "halo" is used herein to describe, unless otherwise stated, a group selected from fluorine ("fluoro"), chlorine ("chloro"), bromine ("bromo") or iodine ("iodo").

The term "naphthyl" is used herein to denote, unless otherwise stated, both naphth-1-yl and naphth-2-yl groups.

The term "pyridyl" includes 2-pyridyl, 3-pyridyl and 4-pyridyl but preferably denotes 2-pyridyl. The term pyrimidinyl includes 2-pyrimidinyl.

The present invention also provides a process for the preparation of a compound of formula (I) or a pharmaceutically acceptable salt or solvate thereof, which process comprises coupling a compound of formula (II):

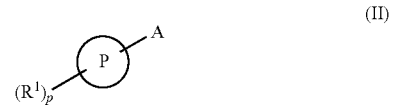

(II)

in which $R^1$, P and p are as defined in formula (I) with a compound of formula (III):

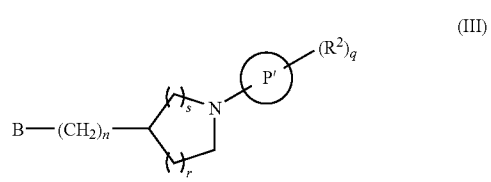

(III)

in which P', $R^2$, n, q, r and s are as defined in formula (I) and A and B contain appropriate functional groups which are capable of reacting together to form the urea moiety;

and thereafter, as necessary, carrying out one or more of the following reactions:

(i) converting one compound of formula (I) into another compound of formula (I);
(ii) removing any protecting group;
(iii) preparing a salt or a solvate of the compound so formed.

Suitable examples of appropriate A and B groups include:
(a) A is —N═C═O and B is NH$_2$; or A is NH$_2$ and B is N═C═O or
(b) A is NH$_2$ and B is NH$_2$ together with an appropriate urea forming agent.

In process (a) the reaction is typically carried out in an inert solvent such as DCM or acetonitrile.

In process (b) the urea forming agent can be carbonyl diimidazole or phosgene or triphosgene, and carried out in an inert organic solvent such as diethyl ether, tetrahydrofuran or DCM at ambient or elevated temperature in the presence of a base such as triethylamine or pyridine.

An alternative method of synthesis of the unsymmetrical urea compounds of formula (I) is from a diaryl carbonate, via the corresponding carbamate. Such a methodology is described by Freer et al. (Synthetic Communications, 26(2), 331-349, 1996). It would be appreciated by those skilled in the art that such a methodology could be readily adapted for preparation of the compounds of formula (I).

A further method of synthesis is using phenyl chloroformate as described by B. R. Baker et al., J. Med. Chem., 1969, 12, 672-6.

A compound of formula (III) may be prepared by reaction of a compound of formula (IV):

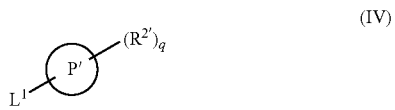

wherein, P', q and R$^2$ are as defined above and L$^1$ is a leaving group, with a compound of formula (V):

wherein B, n, r and s are as defined above or a protected derivative thereof. When B represents an amine group, preferably it is employed as a protected derivative; examples of amine protecting groups are mentioned below.

Preferably L$^1$ is a halogen, such as chlorine.

Suitably, the compound of formula (V) is in an activated form, for example an ionic form. Such activated forms are prepared using conventional coupling reaction methodology, as for example by reacting compounds (IV) and (V) in the presence of an alkali carbonate, such as potassium carbonate, in an aprotic solvent such as dimethylformamide using reaction conditions appropriate to the particular methodology chosen, for example at an elevated temperature, such as 100° C.

Compounds of formulae (IV) and (V) are commercially available, or are prepared by known procedures, such as those disclosed in: *Heterocycles*, 1984, 22(1), 117and J. Chem. Soc., Perkin 1, 1988, 4, .921 for compounds of formula (IV) and *J. Med. Chem.*, 1992, 35(10), 1764 for compounds of formula (V), or by methods analogous to these disclosed methods.

Compounds of formula (II) are either known or may be prepared by known methods, or methods analogous to those described herein.

It will be appreciated by those skilled in the art that it may be necessary to protect certain reactive substituents during some of the above-mentioned procedures. Standard protection and deprotection techniques, such as those described in Greene T. W. 'Protective groups in organic synthesis', New York, Wiley (1981), can be used. For example, primary amines can be protected as phthalimide, benzyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art.

In particular in the reaction of compounds of formula (IV) and (V) the group B preferably represents —NH(t-BOC)—.

Pharmaceutically acceptable salts may be prepared conventionally by reaction with the appropriate acid or acid derivative.

Novel intermediates are claimed as an aspect of the invention.

Compounds of formula (I) and their pharmaceutically acceptable salts or solavtes thereof have Vanilloid receptor antagonist (VR1) activity and are believed to be of potential use for the treatment or prophylaxis of certain disorders, or treatment of the pain associated with them, such as: pain, chronic pain, neuropathic pain, postoperative pain, postrheumatoid arthritic pain, osteoarthritic pain, back pain, visceral pain, cancer pain, algesia, neuralgia, dental pain, headache, migraine, neuropathies, carpal tunnel syndrome, diabetic neuropathy, HIV-related neuropathy, post-herpetic neuralgia, fibromyalgia, neuritis, sciatica, nerve injury, ischaemia, neurodegeneration, stroke, post stroke pain, multiple sclerosis, respiratory diseases, asthma, cough, COPD, broncho constriction, inflammatory disorders, oesophagitis, heart burn, Barrett's metaplasia, dysphagia, gastroeosophageal relux disorder (GERD), stomach and duodenal ulcers, functional dyspepsia, irritable bowel syndrome, inflammatory bowel disease, colitis, Crohn's disease, pelvic hypersensitivity, pelvic pain, menstrual pain, renal colic, urinary incontinence, cystitis, burns, itch, psoriasis, pruritis, emesis (hereinafter referred to as the "Disorders of the Invention").

Accordingly, the invention also provides a compound of formula (I) or a pharmaceutically acceptable salt or solvate thereof, for use as an active therapeutic substance, in particular, in the treatment and/or prophylaxis of the Disorders of the Invention.

In particular, the invention provides a compound of formula (I) or a pharmaceutically acceptable salt or solvate thereof for use in the treatment or prophylaxis of pain.

The invention further provides a method for the treatment or prophylaxis of disorders in which antagonism of the Vanilloid (VR1) receptor is beneficial, in particular the Disorders of the Invention, in mammals including humans, which comprises administering to a mammal in need thereof a therapeutically effective amount of a compound of formula (I) or a pharmaceutically acceptable salt or solvate thereof.

The invention provides for the use of a compound of formula (I) or a pharmaceutically acceptable salt or solvate thereof in the manufacture of a medicament for the treatment or prophylaxis of disorders in which antagonism of the Vanilloid (VR1) receptor is beneficial, particularly the Disorders of the Invention.

In order to use the compounds of the invention in therapy, they will normally be formulated into a pharmaceutical composition in accordance with standard pharmaceutical practice. Thus, the present invention also provides a pharmaceutical composition, which comprises a compound of formula (I) or a pharmaceutically acceptable salt or solvate thereof and a pharmaceutically acceptable carrier or excipient therefor.

A pharmaceutical composition of the invention, which may be prepared by admixture, suitably at ambient temperature and atmospheric pressure, is usually adapted for oral, parenteral, rectal administration or intravesical adminstration to the bladder and, as such, may be in the form of tablets, capsules, oral liquid preparations, powders, granules, lozenges, reconstitutable powders, injectable or infusable solutions, suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. For systemic administration, dosage levels from 0.01 mg to 100 mg per kilogramme of body weight are useful in the treatment of pain. However, as a general guide suitable unit doses may be 0.05 to 1000 mg, more suitably 0.05 to 20, 20 to 250, or 0.1 to 500.0 mg, for example 0.2 to 5 and 0.1 to 250 mg; and such unit doses may be administered more than once a day, for example two or three a day, so that the total daily dosage is in the range of about 0.5 to 1000 mg; and such therapy may extend for a number of weeks or months.

No unacceptable toxicological effects are indicated with compounds of the invention when administered in accordance with the invention.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of the compounds of the invention.

Abbreviations $MgSO_4$—Magnesium sulfate

TFA—Trifluoroacetic acid

DCM—dichloromethane

N,N-DMF—N,N-dimethylformamide t-BOC—t-butoxycarbonyl

DESCRIPTION 1

[(R)-1-(3-Trifluoromethylpyridin-2-yl)pyrrolidin-3-yl]-carbamic acid tert-butyl ester (D1)

To a solution of 2-chloro-3-trifluoromethylpyridine (7.3 g, 0.04 mol) and 3R-(+)-3-(tert-butyloxycarbonylamino)pyrrolidine (7.5 g, 0.04 mol) in dry dimethylformamide (100 ml) was added powdered potassium carbonate (6.6 g, 0.05 mol) and the reaction heated at 100° C. for 7 h and cooled. Solvent was removed under reduced pressure and the residue partitioned between ethyl acetate and water. The organic phase was separated, dried ($MgSO_4$) and filtered. Removal of solvent under reduced pressure gave a solid. Chromatography on silica gel eluting with ethyl acetate and DCM (gradient elution, 20% maximum) afforded the title compound as a white solid.

DESCRIPTION 2

(R)-1-(3-Trifluoromethylpyridin-2-yl)pyrrolidin-3-ylamine (D2)

A solution of D1 (11.5 g, 0.04 mol) in DCM (80 ml) was cooled (ice-bath) and TFA (excess, 50ml) was added. Reaction was warmed to ambient temperature, stirred for 3 h and partitioned between ethyl acetate and aqueous sodium hydroxide. The organic phase was separated, dried ($MgSO_4$) and filtered. Removal of solvent under reduced pressure afforded the crude product as a yellow oil. Bulb to bulb distillation under reduced pressure initially afforded the product as a oil which crystallised on standing.

DESCRIPTION 3

1,3-Dimethyl-5-nitroisoquinoline (D3)

1,3-Dimethylisoquinoline [(*Chem. Lett.*, 1983, p.791), 2.39 g, 15.20 mM], in conc. sulfuric acid, (15 ml), was cooled to below 4° C. A solution of potassium nitrate (1.69 g, 16.72 mM) in conc. sulfuric acid was added dropwise, maintaining the temperature below 4° C. After complete addition the solution was stirred at this temperature for a further 2 h. then warmed to room temperature for 1 h. The reaction mixture was poured into ice water and the solution basified with sodium hydroxide and extracted with DCM. The extract was washed with brine, dried and concentrated to a yellow solid.

Purification by silica gel chromatography afforded the title compound as a yellow crystalline solid.

DESCRIPTION 4

5-Amino-1,3-dimethylisoquinoline (D4)

A solution of D3 (2.01 g, 9.94 mM) and 10% palladium on charcoal (1 g) in methanol was hydrogenated at atmospheric pressure for 1 h. The catalyst was filtered off and the filtrate concentrated under reduced pressure to afford the product as a cream coloured solid.

DESCRIPTION 5

5-Amino-1-methylisoquinoline (D5)

The title compound was prepared in a similar manner to that of K. C. Agrawal, B. A. Booth, A. C. Sartorelli, *J. Med. Chem.*, 1968 11 700.

DESCRIPTION 6

(1-Benzyl-piperidin-4-yl)carbamic acid tert-butyl ester (D6)

To a solution of 1-benzyl-4-aminopiperidine (30 g, 0.16 mol) in DCM (200 ml) was added dropwise a solution of di-tert-butyl dicarbonate (1.1 eq., 37.9 g) in DCM (100 ml) over a period of 2 h. Reaction was stirred at ambient temperature for 18 h and then solvent was removed under reduced pressure to afford the product as a white solid.

DESCRIPTION 7

Piperidin-4-yl-carbamic acid tert-butyl ester (D7)

A solution of D6 (10 g, 3.4 mmol) in methanol (150 ml) was hydrogenated at 50 psi in a Parr hydrogenator using 10% Palladium on carbon catalyst (800 mg) for 18 h. Catalyst was filtered off and the filtrate concentrated under reduced pressure to afford the product as a white solid.

DESCRIPTION 8

1-(5-Trifluoromethylpyridin-2-yl)piperidin-4-ylamine (D8)

The title compound was prepared from D7 and 2-chloro-5-ifluoromethylpyridine using the procedure outlined for Descriptions D1 and D2.

DESCRIPTION 9

(R)-1-(6-Trifluoromethylpyridin-2-yl)pyrrolidin-3-ylamine(D9)

The title compound was prepared from 2-chloro-6-trifluoromethylpyridine and 3R-(+)-3-(tert-butyloxycarbonylamino)pyrrolidine using the procedure outlined for Descriptions D1 and D2.

DESCRIPTION 10

(R)-1-(3-Chloropyridin-2-yl)pyrrolidin-3-ylamine (D10)

The title compound was prepared from 2,3-dichloropyridine and 3R-(+)-3-(tert-butyloxycarbonylamino)pyrrolidine using the procedure outlined for Descriptions D1 and D2.

DESCRIPTION 11

1-(3-Chloro-5-trifluoromethylpyridin-2-yl)piperidin-4-yl-carbamic acid-tert-butyl ester (D11)

A stirred suspension of D7 (5.5 g, 27.5 mmol), 3,6-dichloro-5-trifluoromethylpyridine (3.83 mL, 27.5 mmol) (for synthesis see *Tetrahedron*, 1985, 41, 4057) and potassium carbonate (11.4 g, 82.6 mmol) in dry N,N-DMF (100 mL) was heated at 120° C. for 24 h. After cooling to ambient temperature, the mixture was poured into water (1 L), stirred for 1 h and then filtered. The residue was washed with water (3×150 mL and dried (MgSO$_4$) to afford the title compound (9.8 g).

DESCRIPTION 12

1-(3-Chloro-5-trifluoromethylpyridin-2-yl)piperidin-4-ylamine (D12)

Trifluoroacetic acid (20 mL) was slowly added to a stirred solution of D11 (9.8 g, 25.8 mmol) in DCM (60 mL) at ambient temperature. After stirring for 5 h, the solution was adjusted to pH 14 by the slow addition of 1M KOH solution. The heterogeneous mixture was then separated and the aqueous phase saturated with sodium chloride and further extracted with DCM (5×75 mL). The combined organic extracts were dried (MgSO$_4$) and concentrated in vacuo to an oil. The oil was stirred with diethyl ether (50 mL) for 0.5 h to give the title compound as a white solid (7.3 g).

Mass Spectrum: $C_{11}H_{13}{}^{35}ClF_3N_3$ requires 279. Found 280 (MH$^+$).

DESCRIPTION 13

1-(6-Chloro-5-trifluoromethylpyridin-2-yl)piperidin-4-yl-carbamic acid tert-butyl ester (D13)

A stirred mixture of D7 (5.0 g, 25 mmol), 2,6-dichloro-3-trifluoromethyl-pyridine (5.4 g, 25 mmol) and cesium carbonate (12.22 g, 37.5 mmol) in 1,4-dioxane (75 mL) was heated at reflux under argon for 64 h. To the mixture, which was cooled to ambient temperature, was added water (250 mL) and DCM (250 mL) with shaking and the layers were separated. The aqueous phase was further extracted with DCM (250 mL) and the combined organic extracts were dried (MgSO$_4$) and evaporated in vacuo to an oil. This material was purified by chromatography over silica gel eluting with a gradient of ethyl acetate/hexane to afford the title compounds (5.0 g, 13.2 mmol, 53%). Mass Spectrum: $C_{16}H_{21}{}^{35}ClF_3N_3O_2$ requires 379. Found 380 (MH$^+$).

DESCRIPTION 14

1-(6-Methoxy-5-trifluoromethylpyridin-2-yl)piperidin-4-ylamine (D14)

A sodium methoxide solution (25% wt/vol, 2.79 mL, 12.2 mmol) was added to a stirred solution of D13 (1.55 g, 4.07 mmol) in 1,2-dimethoxyethane (30 mL) under argon. The mixture was then refluxed under argon for 28 h. After cooling to ambient temperature, the solvent was evaporated in vacuo and the residue was dissolved in water (50 mL). This solution was extracted with DCM (3×30 mL) and the combined organic extracts were dried (MgSO$_4$) and evaporated in vacuo to an oil. The oil was purified by chromatography on silica gel eluting with a gradient of ethyl acetate/hexane followed by DCM/methanol to afford the title compound (0.34 g).

Mass Spectum: $C_{12}H_{16}F_3N_3O$ requires 275. Found 276 (MH$^+$).

DESCRIPTION 15

1-(3-Trifluoromethylpyridin-2-yl)piperidine-4-ylamine (D15)

The title compound was prepared from D7 and 2-chloro-3-trifluoromethyl-pyridine using the procedure outlined for Descriptions D11 and D12.

DESCRIPTION 16

1-(6-Trifluoromethylpyridin-2-yl)piperidin-4-ylamine(D16)

The title compound was prepared from D7 and 2-chloro-6-trifluoromethyl-pyridine using the procedure outlined for Descriptions D11 and D12.

DESCRIPTION 17

1-(4-Trifluoromethylpyridin-2-yl)piperidin-4-ylamine(D17)

The title compound was prepared from D7 and 2-chloro-4-trifluoromethyl-pyridine using the procedure outlined for Descriptions D11 and D12.

DESCRIPTION 18

1-(4-Trifluoromethylpyrimidin-2-yl)piperidin-4-ylamine (D18)

The title compound was prepared from D7 and 2-chloro-4-trifluoromethyl-pyrimidine using the procedure outlined for Descriptions D11 and D12.

The following amines were prepared using methods similar to those described above:

(R)-1-(6-Methyl-5-trifluoromethylpyridin-2-yl)pyrrolidin-3-ylamine (D19).
(R)-1-(6-Methyl-4-trifluoromethylpyridin-2-yl)pyrrolidin-3-ylamine (D20).
(R)-1-(6-Methyl-3-trifluoromethylpyridin-2-yl)pyrrolidin-3-ylamine (D21).
(R)-1-(3-Chloro-5-trifluoromethylpyridin-2-yl)pyrrolidin-3-ylamine (D22).
(R)-1-(3-Bromo-5-trifluoromethylpyridin-2-yl)pyrrolidin-3-ylamine (D23).
1-(3-Chloropyridin-2-yl)piperidin-4-ylamine (D24).
1-(6-Methoxypyridin-2-yl)piperidin-4-ylamine (D25).
1-(6-Methyl-5-trifluoromethylpyridin-2-yl)piperidin-4-ylamine (D26).
1-(6-Methyl-4-trifluoromethylpyridin-2-yl)piperidin-4-ylamine (D27).
1-(3-Methyl-5-trifluoromethylpyridin-2-yl)piperidin-4-ylamine (D28).
1-(3-Bromo-5-trifluoromethylpyridin-2-yl)piperidin-4-ylamine (D29).
1-(3-Chloro-6-trifluoromethylpyridin-2-yl)piperidin-4-ylamine (D30).
1-(5-Chloro-6-trifluoromethylpyridin-2-yl)piperidin-4-ylamine (D31).
1-(3-Chloro-6-methoxypyridin-2-yl)piperidin-4-ylamine (D32).
1-(6-Methoxy-3-trifluoromethylpyridin-2-yl)piperidin-4-ylamine (D33).
1-(3-[4-Fluorophenyl]-5-trifluoromethylpyridin-2-yl)piperidin-4-ylamine (D34).

1-(3,4-Difluorophenvl)piperidin-4-ylamine (D35).

This compound was prepared using methodology described in WO 02/090326 and D2.

(R)-1-(5-Bromopyridin-2-yl)pyrrolidin-3-ylamine (D36).

This compound was prepared by a process analogous to that described in D1 and D2.

(R)-1-(6-Methoxypyridin-2-yl)pyrrolidin-3-ylamine (D37).
(R)-1-(4-Trifluoromethylpyridin-2-yl)pyrrolidin-3-ylamine (D38).
(R)-1-(5-Chloro-6-trifluoromethylpyridin-2-yl)pyrrolidin-3-ylamine (D39).
(R)-1-(3-Chloro-6-methoxypyridin-2-yl)pyrrolidin-3-ylamine (D40).
(R)-1-(3-Methyl-5-trifluoromethylpyridin-2-yl)pyrrolidin-3-ylamine (D41).
1-(5-Chloro-6-methoxypyridin-2-yl)piperidin-4-ylamine (D42).

(R)-1-(4-Trifluoromethylthiazol-2-yl)pyrrolidin-3-ylamine (D43).

Prepared from 2-bromo4-trifluoromethylthiazole (J. A. Edwards Ger. Offen., 2252070, 1973) in a manner similar to that described in D1 and D2.

1-(4-Trifluoromethylthiazol-2-yl)piperidin-4-ylamine (D44).

Prepared from D8 and 2-bromo4-trifluoromethylthiazole (J. A. Edwards Ger. Offen., 2252070, 1973) in a manner similar to that described in D1 and D2. The following were prepared using methods described above and in a manner similar to that of D18:

1-(2-Trifluoromethylpyrimidin-4-yl)piperidin-4-ylamine (D45)
1-(6-Trifluoromethylpyridin-3-yl)piperidin-4-ylamine (D46).
1-(2-Trifluoromethylpyridin-4-yl)piperidin-4-ylamine (D46).
1-(6-Methyl-4-N-morpholinylmethylpyridin-2-yl)piperidin-4-ylamine (D47)

EXAMPLE 1

1-([3-Chloro-5-trifluoromethylpyridinyl-2-yl]piperidin-4-yl)-3-(1-methyl-isoquinolin-5-yl)-urea hydrochloride (E1)

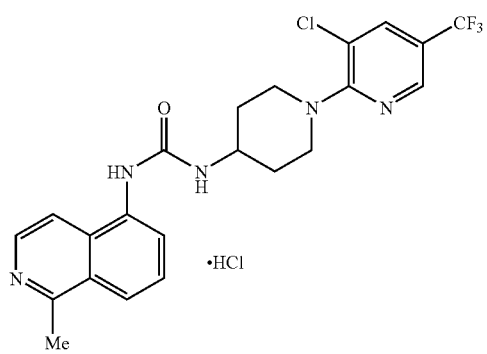

Phenyl chloroformate (0.87 mL, 7.0 mmol) was added dropwise to a stirred solution of D5 (1.0 g, 6.32 mmol) and pyridine (0.56 mL, 7.0 mmol) in DCM (20 mL) at room temperature under argon. After 2 h, triethylamine (1.85 mL, 13.3 mmol) was added dropwise. After a further 10 minutes at room temperature, a solution of D12 (1.77 g, 6.32 mmol) in dichloromethane (10 mL) was added dropwise and the mixture was stirred for 18 h. The precipitated solid was collected and washed successively with dichloromethane (3×5 mL), diethyl ether (5 mL), water (3×5 mL) and converted into the corresponding hydrochloride salt by adding a 1 M HCl in diethyl ether (8.5 mL) to a suspension of the solid in methanol (100 mL). After diluting the resulting solution with diethyl ether (50 mL) and ice cooling, the resultant yellow solid was collected and gave the title compound (1.1 g).

$\delta_H$:(400 MHz, DMSO-$d_6$) 1.56-1.65 (2H, m), 2.01-2.03 (2H,m), 3.16 (3H, s), 3.16-3.22 (2H, m), 3.85-3.93 (3H, m), 7.22 (1H, d, J=7.5 Hz), 7.92 (1H, m), 8.16-8.18 (2H, m), 8.56 (3H, br s), 8.63 (1H, d, J=7.8 Hz), 9.28 (1H, s).

Mass Spectum: $C_{22}H_{21}{}^{35}ClF_3N_5O$ requires 463. Found 464 (MH$^+$).

EXAMPLE 2

1-([6-Methoxy-5-trifluoromethylpyridinyl-2-yl]piperidin-4-yl)-3-(1-methyl-isoquinolin-5-yl)-urea hydrochloride (E2)

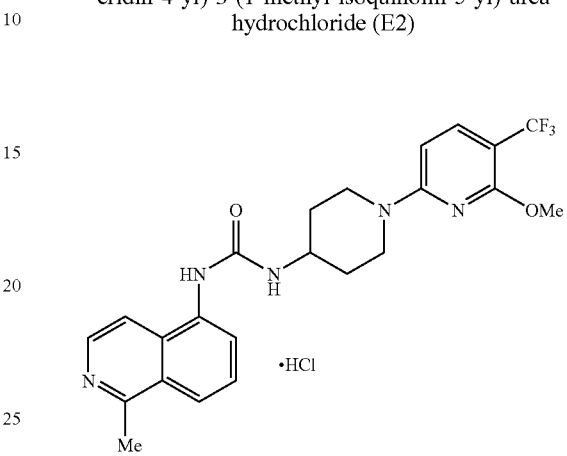

The title compound was prepared using the method of E1 from D14 (0.11 g, 0.4 mmol) and D5 (63 mg, 0.4 mmol).

$\delta_H$:(400 MHz, CD$_3$OD) 1.50-1.60 (2H, m), 2.06-2.10 (2H, m), 3.13-3.26 (2H, m), 3.23 (3H, s), 3.91-3.98 (4H, m), 4.36-4.39 (2H, m), 6.34 (1H, d, J=8.6 Hz), 8.00 (1H, dd, J=J=7.9 Hz), 8.33-8.43 (4H, m).

Mass Spectum: $C_{23}H_{21}F_3N_5O_2$ requires 459; Found 460 (MH$^+$).

The following Examples detailed in Table 1 below were prepared using similar methods to those described above. n has the value 0 in all cases.

TABLE 1

| Ex | P (R$^1$)$_p$ | S'Chem | s | r | P' (R$^2$)$_q$ | MH+ |
|---|---|---|---|---|---|---|
| 3 | 5-methyl-1-methylisoquinoline | R | 1 | 1 | 3-CF$_3$-2-methylpyridine | 416 |

TABLE 1-continued
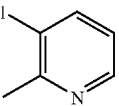
| Ex | P (R¹)ₚ | S'Chem | s | r | P' (R²)_q | MH+ |
|---|---|---|---|---|---|---|
| 4 | 5-methylisoquinolin-1-yl (1-Me) | R | 1 | 1 | 3-Cl, 2-Me pyridine | 382, 384 |
| 5 | 5-methylisoquinolin-1-yl (1-Me) | R | 1 | 1 | 3-CF₃, 2,6-diMe pyridine | 430 |
| 6 | 5-methylisoquinolin-1-yl (1-Me) | R | 1 | 1 | 3-Cl, 5-CF₃, 2-Me pyridine | 450, 452 |
| 7 | 5-methylisoquinolin-1-yl (1-Me) | R | 1 | 1 | 3-CF₃, 2,6-diMe pyridine | 430 |
| 8 | 5-methylisoquinolin-1-yl (1-Me) | R | 1 | 1 | 3-Br, 5-CF₃, 2-Me pyridine | 494, 496 |
| 9 | 5-methylisoquinolin-1-yl (1-Me) | R | 1 | 1 | 4-CF₃, 2,6-diMe pyridine | 430 |

TABLE 1-continued

| Ex | (R¹)ₚ ⓟ | S'Chem | s | r | (R²)_q ⓟ' | MH+ |
|---|---|---|---|---|---|---|
| 10 | 3,5-dimethyl-isoquinolin-1-yl (Me at 1 and 3 positions of isoquinoline) | R | 1 | 1 | 3-Cl, 2-Me pyridine | 396, 398 |
| 11 | 3,5-dimethyl-isoquinolin-1-yl | R | 1 | 1 | 6-Me, 2-CF₃ pyridine | 430 |
| 12 | 3,5-dimethyl-isoquinolin-1-yl | R | 1 | 1 | 3-Cl, 5-CF₃, 2-Me pyridine | 464, 466 |
| 13 | 3,5-dimethyl-isoquinolin-1-yl | R | 1 | 1 | 3-CF₃, 2,6-diMe pyridine | 444 |
| 14 | 3,5-dimethyl-isoquinolin-1-yl | R | 1 | 1 | 4-CF₃, 2,6-diMe pyridine | 444 |
| 15 | 3,5-dimethyl-isoquinolin-1-yl | R | 1 | 1 | 3-CF₃, 2,6-diMe pyridine | 444 |

TABLE 1-continued

| Ex | P(R¹)ₚ | S'Chem | s | r | P'(R²)q | MH+ |
|---|---|---|---|---|---|---|
| 16 | 5-Me, 3-Me, 1-Me isoquinoline | R | 1 | 1 | 2-Me, 5-Br pyridine | 440, 442 |
| 17 | 5-Me, 1-Me isoquinoline | — | 2 | 1 | 2-Me, 4-CF₃ pyrimidine | 431 |
| 18 | 5-Me, 1-Me isoquinoline | — | 2 | 1 | 2-Me, 6-CF₃ pyridine | 430 |
| 19 | 5-Me, 1-Me isoquinoline | — | 2 | 1 | 3-CF₃, 2-Me pyridine | 430 |
| 20 | 5-Me, 1-Me isoquinoline | — | 2 | 1 | 4-CF₃, 2-Me pyridine | 430 |
| 21 | 5-Me, 1-Me isoquinoline | — | 2 | 1 | 3-Cl, 2-Me pyridine | 396, 398 |

TABLE 1-continued (I)

| Ex | P (R¹)ₚ | S'Chem | s | r | P' (R²)_q | MH+ |
|----|---------|--------|---|---|-----------|-----|
| 22 | 5-Me-isoquinolin-1-yl, 1-Me | — | 2 | 1 | 6-Me-2-OMe-pyridin-3-yl | 392 |
| 23 | 5-Me-isoquinolin-1-yl, 1-Me | — | 2 | 1 | 2,6-diMe-3-CF₃-pyridin-4-yl (2-Me, 6-Me, 3-CF₃) | 444 |
| 24 | 5-Me-isoquinolin-1-yl, 1-Me | — | 2 | 1 | 2,6-diMe-4-CF₃-pyridin-3-yl | 444 |
| 25 | 5-Me-isoquinolin-1-yl, 1-Me | — | 2 | 1 | 3-Br-2-Me-5-CF₃-pyridin-4-yl | 508, 510 |
| 26 | 5-Me-isoquinolin-1-yl, 1-Me | — | 2 | 1 | 2,3-diMe-5-CF₃-pyridin-4-yl | 444 |
| 27 | 5-Me-isoquinolin-1-yl, 1-Me | — | 2 | 1 | 3-Cl-2-Me-6-CF₃-pyridin-4-yl | 464, 466 |

TABLE 1-continued (I)

| Ex | (R¹)ₚ / P | S'Chem | s | r | P' (R²)q | MH+ |
|---|---|---|---|---|---|---|
| 28 | 1-Me-isoquinolin-5-yl | — | 2 | 1 | 3-Cl, 6-Me, 2-CF₃-pyridine | 464, 466 |
| 29 | 1-Me-isoquinolin-5-yl | — | 2 | 1 | 3-Cl, 6-Me, 2-OMe-pyridine (shown as 5-Cl,6-Me,2-OMe) | 426, 428 |
| 30 | 1-Me-isoquinolin-5-yl | — | 2 | 1 | 3-CF₃, 6-Me, 2-OMe-pyridine | 460 |
| 31 | 1-Me-isoquinolin-5-yl | — | 2 | 1 | 3,4-diF-phenyl (with Me) | 397 |
| 32 | 1-Me-isoquinolin-5-yl | — | 2 | 1 | 3-(p-F-Ph), 5-CF₃, 2-Me-pyridine | 524 |
| 33 | 1,3-diMe-isoquinolin-5-yl | — | 2 | 1 | 3-CF₃, 2-Me-pyridine | 444 |

TABLE 1-continued

| Ex | (R¹)ₚ | S'Chem | s | r | (R²)q P' | MH+ |
|---|---|---|---|---|---|---|
| 34 | 3,5-dimethyl-isoquinolin-1-yl (Me at 1, Me at 3, substituent at 5) | — | 2 | 1 | 2-methyl-6-(trifluoromethyl)pyridin-4-yl | 444 |
| 35 | 3,5-dimethyl-isoquinolin-1-yl | — | 2 | 1 | 2-methoxy-6-methylpyridin-4-yl | 406 |
| 36 | 3,5-dimethyl-isoquinolin-1-yl | — | 2 | 1 | 2,6-dimethyl-4-(trifluoromethyl)pyridin-3-yl | 458 |
| 37 | 1,5-dimethyl-isoquinolin-5-yl | R | 1 | 1 | 2-methyl-3-methyl-5-(trifluoromethyl)pyridin-? | 430 |
| 38 | 1,5-dimethyl-isoquinolin-5-yl | R | 1 | 1 | 3-chloro-6-methyl-2-(trifluoromethyl)pyridin-4-yl | 450, 452 |
| 39 | 1,5-dimethyl-isoquinolin-5-yl | R | 1 | 1 | 5-bromo-2-methylpyridin-? | 426, 428 |

TABLE 1-continued

| Ex | (R¹)ₚ / P | S'Chem | s | r | P' / (R²)_q | MH+ |
|---|---|---|---|---|---|---|
| 40 | 5-Me-1-Me-isoquinoline | R | 1 | 1 | 3-Cl-6-methyl-2-OMe-pyridine (Cl up, Me down) | 412, 414 |
| 41 | 5-Me-1-Me-isoquinoline | R | 1 | 1 | 3-Cl-6-methyl-2-OMe-pyridine | 412, 414 |
| 42 | 5-Me-1-Me-isoquinoline | R | 1 | 1 | 6-methyl-2-OMe-pyridine | 378 |
| 43 | 5-Me-1-Me-isoquinoline | R | 1 | 1 | 4-CF₃-2-methyl-pyridine | 416 |
| 44 | 5-Me-1-Me-isoquinoline | R | 1 | 1 | 2-methyl-4-CF₃-thiazole | 422 |
| 45 | 5-Me-1-Me-isoquinoline | — | 2 | 1 | 3-Cl-6-methyl-2-OMe-pyridine | 426, 428 |

TABLE 1-continued

| Ex | (R¹)ₚ | S'Chem | s | r | P'(R²)q | MH+ |
|---|---|---|---|---|---|---|
| 46 | 5-methyl-1-methylisoquinoline | — | 2 | 1 | 2-methyl-4-(trifluoromethyl)thiazole | 436 |
| 47 | 1,3-dimethyl-5-methylisoquinoline | R | 1 | 1 | 2,3-dimethyl-5-(trifluoromethyl)pyridine | 444 |
| 48 | 1,3-dimethyl-5-methylisoquinoline | R | 1 | 1 | 3-chloro-6-methyl-2-(trifluoromethyl)pyridine | 464, 466 |
| 49 | 1,3-dimethyl-5-methylisoquinoline | R | 1 | 1 | 3-chloro-6-methoxy-2-methylpyridine | 426, 428 |
| 50 | 1,3-dimethyl-5-methylisoquinoline | R | 1 | 1 | 3-chloro-2-methoxy-6-methylpyridine | 426, 428 |
| 51 | 1,3-dimethyl-5-methylisoquinoline | R | 1 | 1 | 2-methyl-4-(trifluoromethyl)thiazole | 436 |

TABLE 1-continued (I)

| Ex | (R¹)ₚ | S'Chem | s | r | (R²)q | MH+ |
|---|---|---|---|---|---|---|
| 52 | 3,5-dimethyl-1-methylisoquinoline (Me, Me) | — | 2 | 1 | 2-methyl-4-(trifluoromethyl)pyrimidine | 445 |
| 53 | 3,5-dimethyl-1-methylisoquinoline | — | 2 | 1 | 3-chloro-2-methyl-5-(trifluoromethyl)pyridine | 478, 480 |
| 54 | 3,5-dimethyl-1-methylisoquinoline | — | 2 | 1 | 6-methoxy-2-methylpyridine | 406 |
| 55 | 3,5-dimethyl-1-methylisoquinoline | — | 2 | 1 | 3-bromo-2-methyl-5-(trifluoromethyl)pyridine | 522, 524 |
| 56 | 3,5-dimethyl-1-methylisoquinoline | — | 2 | 1 | 3-chloro-6-methoxy-2-methylpyridine | 440, 442 |
| 57 | 3,5-dimethyl-1-methylisoquinoline | — | 2 | 1 | 3-chloro-2-methoxy-6-methylpyridine | 440, 442 |

TABLE 1-continued
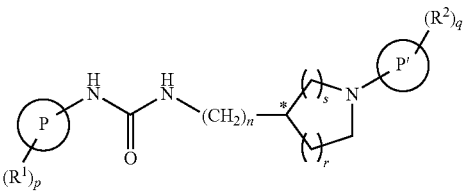
(I)
| Ex | P (R¹)p | S'Chem | s | r | P' (R²)q | MH+ |
|---|---|---|---|---|---|---|
| 58 | 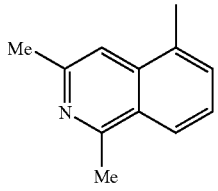 | — | 2 | 1 | 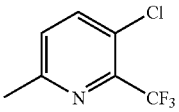 | 478, 480 |
| 59 | 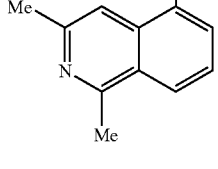 | — | 2 | 1 | 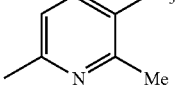 | 458 |
| 60 | 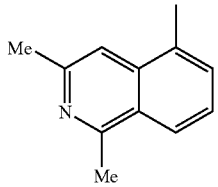 | — | 2 | 1 | 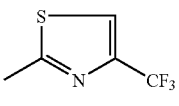 | 450 |
| 61 | 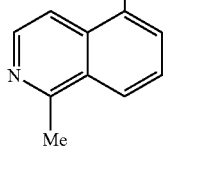 | R | 1 | 1 | 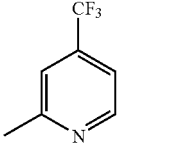 | 416 |
| 62 | 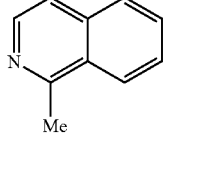 | — | 2 | 1 | 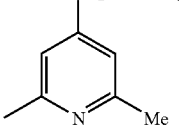 CH₂—N-morpholine | 475 |
| 63 | 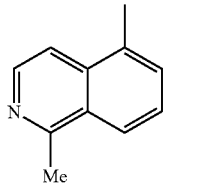 | — | 2 | 1 | 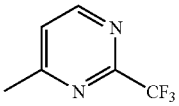 | 431 |

TABLE 1-continued

| Ex | (R¹)ₚ / P | S'Chem | s | r | P' / (R²)_q | MH+ |
|---|---|---|---|---|---|---|
| 64 | 5-methyl-1-methylisoquinoline | — | 2 | 1 | 5-methyl-2-(CF₃)-pyridine | 430 |
| 65 | 5-methyl-1-methylisoquinoline | — | 2 | 1 | 4-methyl-2-(CF₃)-pyridine | 430 |
| 66 | 3,5-dimethyl-1-methylisoquinoline | — | 2 | 1 | 2,6-dimethyl-4-(CH₂-N-morpholine)-pyridine | 489 |
| 67 | 3,5-dimethyl-1-methylisoquinoline | — | 2 | 1 | 4-methyl-2-(CF₃)-pyrimidine | 445 |
| 68 | 3,5-dimethyl-1-methylisoquinoline | — | 2 | 1 | 5-methyl-2-(CF₃)-pyridine | 444 |
| 69 | 3,5-dimethyl-1-methylisoquinoline | — | 2 | 1 | 4-methyl-2-(CF₃)-pyridine | 444 |

S'Chem = stereochemistry

Pharmacological Data (a) In vitro assay

As referenced above, the compounds of the invention are vanilloid receptor (VR1) antagonists and hence have useful pharmaceutical properties. Vanilloid receptor (VR1) antagonist activity can be confirmed and demonstrated for any particular compound by use of conventional methods, for example those disclosed in standard reference texts such as D. Le Bars, M. Gozarin and S. W. Cadden, Pharmacological Reviews, 2001, 53(4), 597-652] or such other texts mentioned herein.

The screen used for the compounds of this invention was based upon a FLIPR based calcium assay, similar to that described by Smart et al. (British Journal of Pharmacology, 2000, 129, 227-230). Transfected astrocytoma 1321N1 cells, stably expressing human VR1, were seeded into FLIPR plates at 25,000cells/well (96-well plate) and cultured overnight.

The cells were subsequently loaded in medium containing 4 μM Fluo-3 AM (Molecular Probes) for 2 hours, at room temperature, in the dark. The plates were then washed 4 times with Tyrode containing 1.5 mM calcium, without probenecid. The cells were pre-incubated with compound or buffer control at room temperature for 30 minutes. Capsaicin (Sigma) was then added to the cells. Compounds having antagonist activity against the human VR1 were identified by detecting differences in fluorescence when measured after capsaicin addition, compared with no compound buffer controls. Thus, for example, in the buffer control capsaicin addition results in an increase in intracellular calcium concentration resulting in fluorescence. A compound having antagonist activity blocks the capsaicin binding to the receptor, there is no signalling and therefore no increase in intracellular calcium levels and consequently lower fluorescence. pKb values are generated from the $IC_{50}$ values using the Cheng-Prusoff equation.

All compounds (Examples 1-69) tested by the above methodology had pKb>6, preferred compounds (Examples 1, 2, 5, 12, 18, 19, 23, 24, 27, 28, 31, 34, 36, 52 and 58 especially examples 1, 2 and 18) having a pKb>7.0

(b) FCA-induced hyperalgesia in the Guinea pig

100 μl of 1 mg/ml FCA was injected intraplantar into the left paw of 4 groups of 8 male Dunkin Hartley guinea-pigs (batch: 6282434, average weight 340 g). 24 hours later compounds were administered orally at 0 (vehicle), 3, 10 30 mg/kg with vehicle as 1% methylcellulose and dosing volume being 2 ml/kg and dosing straight into the stomach. The methylcellulose was added gradually to the compound into the pestle and mortar and ground together.

Behavioural readouts of mechanical hyperalgesia were obtained before FCA administration (naïve reading), after FCA but before drug administration (predose reading) and 1 hour after drug administration. The readout used was paw pressure (Randall-Sellito) and the end point was paw withdrawal. The paw pressure equipment also had one silver disc placed on the point to increase the markings by a factor of 2.

Compounds having a pKb>7.0 in vitro, according to model (a) above, were tested in this model and shown to be active.

The invention claimed is:

1. A compound having the following formula:

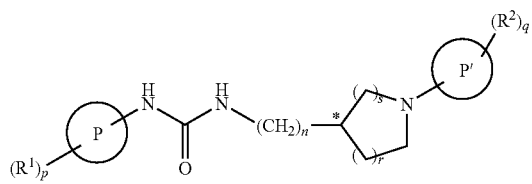

or a pharmaceutically acceptable salt thereof, wherein

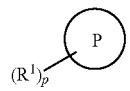

is 1-methyl-5-isoquinolinyl or 1,3-dimethyl-5-isoquinolinyl;

P' is 2-pyridyl;

$R^2$ is Cl, Br, $CF_3$, $OCH_3$, $CH_3$, or p-fluorophenyl;

n is 0;

q is 1 or 2;

r is 1; and s is 2.

2. A composition comprising the compound of claim 1 or a pharmaceutically acceptable salt thereof and a pharmaceutically acceptable excipient or carrier therefor.

3. The compound of claim 1 or a pharmaceutically acceptable salt thereof wherein

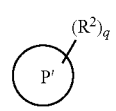

is selected from the group consisting of 3-chloro-5-trifluoromethyl-2-pyridyl; 6-methoxy-3-trifluoromethyl-2-pyridyl; 6-trifluoromethyl-2-pyridyl; 3-trifluoromethyl-2-pyridyl; 4-trifluoromethyl-2-pyridyl; 3-chloro-2-pyridyl; 6-methoxy-2-pyridyl; 6-methyl-5-trifluoromethyl-2-pyridyl; 6-methyl-4-trifluoromethyl-2-pyridyl; 3-bromo-5-trifluoromethyl-2-pyridyl; 3-methyl-5-trifluoromethyl-2-pyridyl; 3-chloro-6-trifluoromethyl-2-pyridyl; 5-chloro-6-trifluoromethyl-2-pyridyl; 3-chloro-6-methoxy-2-pyridyl; 6-methoxy-3-trifluoromethyl-2-pyridyl; and 3-p-fluorophenyl-5-trifluoromethyl-2-pyridyl.

4. The compound of claim 1 or a pharmaceutically acceptable salt thereof wherein

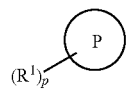

is 1-methyl-5-isoquinolinyl.

5. The compound of claim 1 or a pharmaceutically acceptable salt thereof wherein

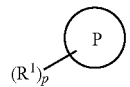

is 1,3-dimethyl-5-isoquinolinyl.

6. The compound of claim 1 or a pharmaceutically acceptable salt thereof which compound is selected from the group consisting of:

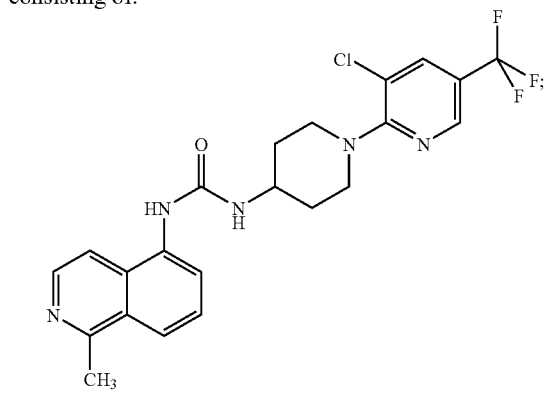

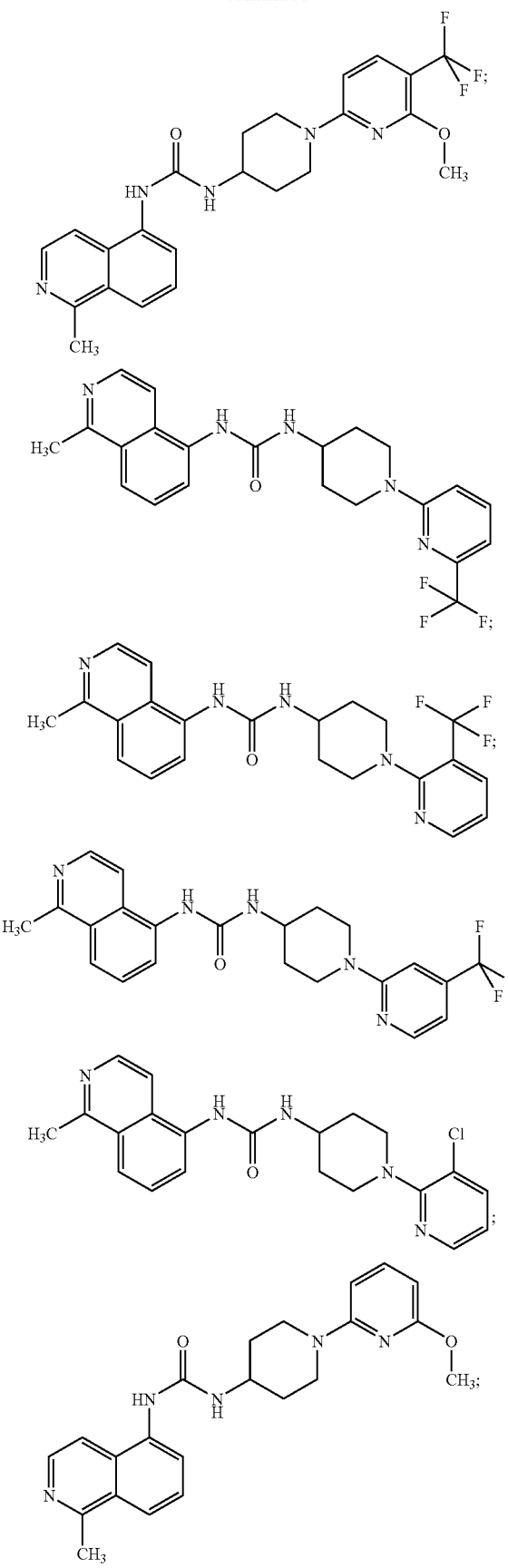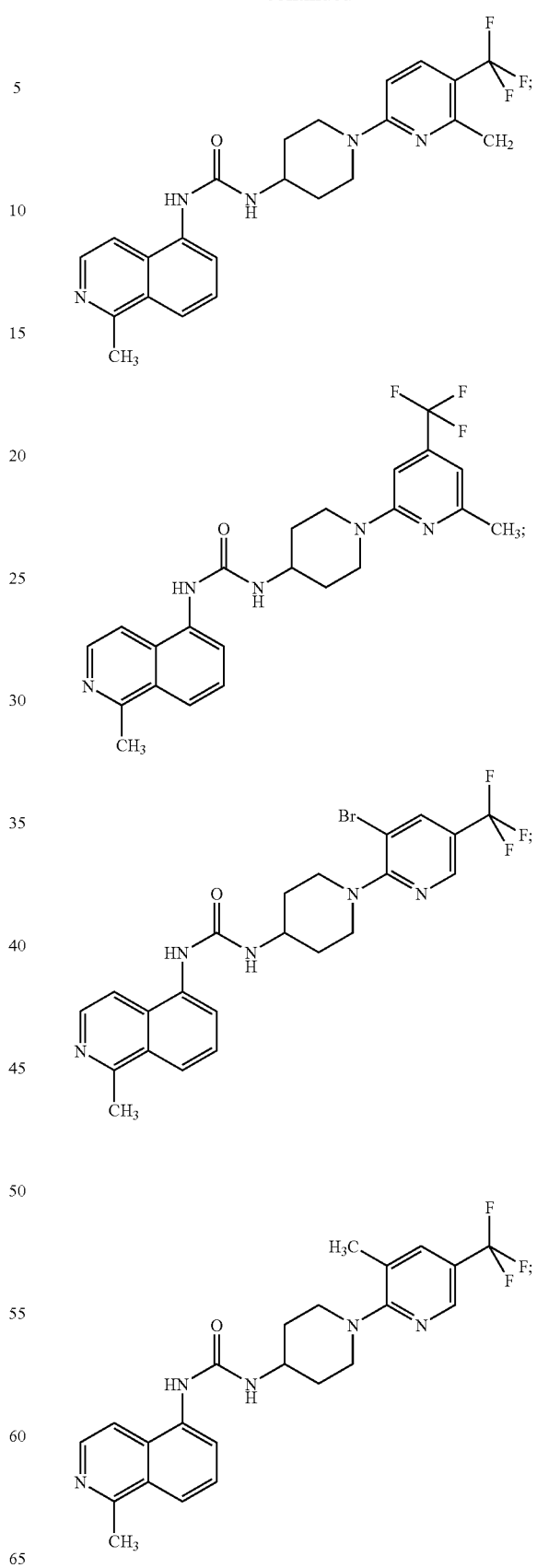

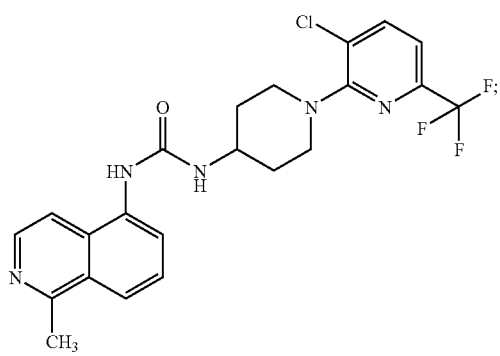
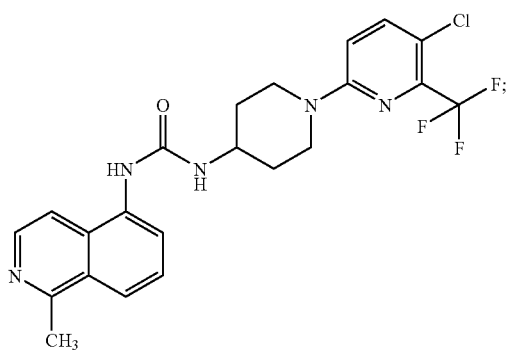
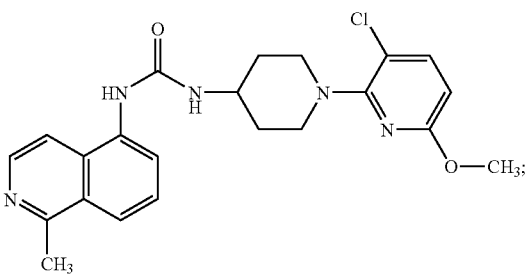
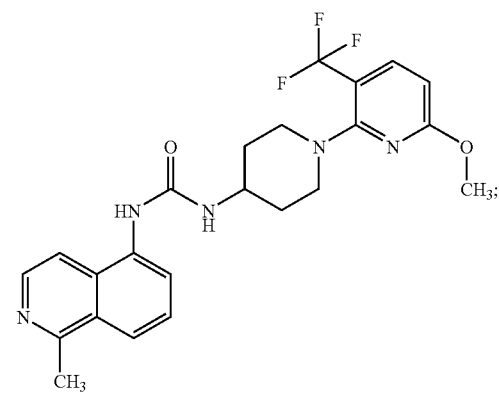
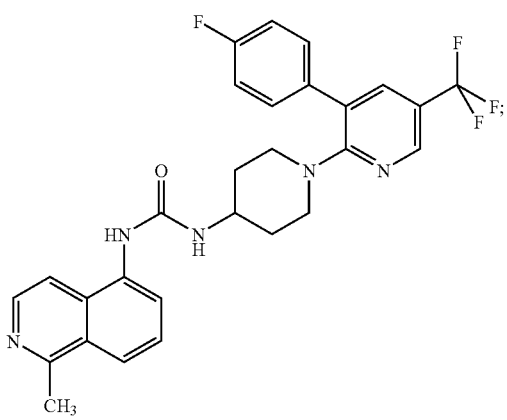
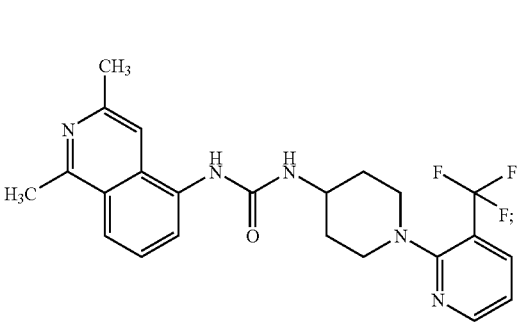
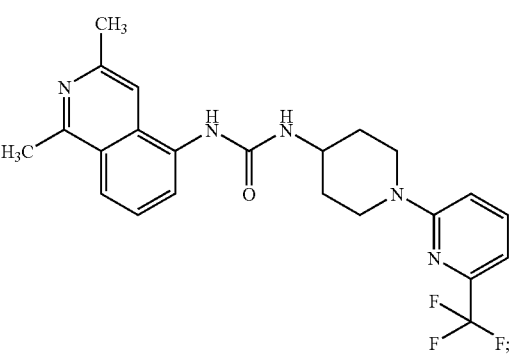

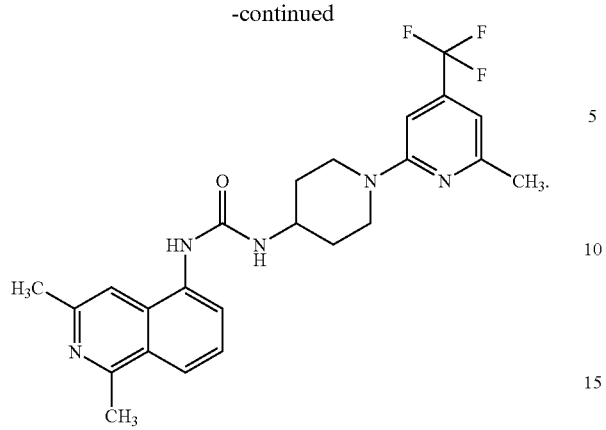
* * * * *